(12) United States Patent
James

(10) Patent No.: US 11,540,648 B2
(45) Date of Patent: Jan. 3, 2023

(54) INFANT, TODDLER AND CHILD SENSORY ENHANCING BED

(71) Applicant: Anisa DeNeen Mosely James, Houston, TX (US)

(72) Inventor: Anisa DeNeen Mosely James, Houston, TX (US)

( * ) Notice: Subject to any disclaimer, the term of this patent is extended or adjusted under 35 U.S.C. 154(b) by 188 days.

(21) Appl. No.: 14/585,816

(22) Filed: Dec. 30, 2014

(65) Prior Publication Data
US 2021/0212477 A1    Jul. 15, 2021

(51) Int. Cl.
| | | |
|---|---|---|
| A47D 7/00 | (2006.01) | |
| A47D 9/02 | (2006.01) | |
| A61M 21/02 | (2006.01) | |
| A47D 15/00 | (2006.01) | |
| A61M 21/00 | (2006.01) | |

(52) U.S. Cl.
CPC .............. *A47D 7/007* (2013.01); *A47D 9/02* (2013.01); *A47D 15/008* (2013.01); *A61M 21/02* (2013.01); *A61M 2021/0027* (2013.01); *A61M 2021/0044* (2013.01); *A61M 2021/0066* (2013.01)

(58) Field of Classification Search
CPC ........ A47D 7/007; A47D 9/02; A47D 15/008; A61M 21/02; A61M 2021/0044; A61M 2021/0027; A61M 2021/0066; A47C 29/003; A47C 17/50; A63F 2009/0056
USPC .................................................... 600/21-22
See application file for complete search history.

(56) References Cited

U.S. PATENT DOCUMENTS

| | | | | |
|---|---|---|---|---|
| 3,656,195 | A * | 4/1972 | Leahey | A47D 7/002 5/99.1 |
| 3,821,822 | A * | 7/1974 | Borreggine | A47D 7/00 5/109 |
| 5,088,138 | A * | 2/1992 | Munster | A47D 9/02 5/101 |
| 5,206,733 | A * | 4/1993 | Holdredge | A47B 23/007 348/836 |
| 5,566,413 | A * | 10/1996 | Webb | A47D 15/008 5/118 |
| 6,682,495 | B2 | 1/2004 | Park | |
| 7,290,300 | B1 * | 11/2007 | Khambete | A47C 7/74 297/180.13 |
| 7,478,446 | B2 | 1/2009 | Sims, Jr. | |
| 7,669,927 | B1 * | 3/2010 | Zaid | A47D 9/02 297/260.2 |
| 2004/0082261 | A1 * | 4/2004 | Bapst | A47D 15/00 446/227 |
| 2007/0063558 | A1 * | 3/2007 | Stewart | A47C 3/029 297/260.2 |

(Continued)

*Primary Examiner* — Kaylee R Wilson
(74) *Attorney, Agent, or Firm* — Greenberg Traurig, LLP; Dwayne Mason; Matthew Browning

(57) ABSTRACT

A bed shaped device or structure provides sensory enhancement for the comfort of the infant, baby, toddler, or child. The invention replicates the physical, physiology, and sensation of the mother to the child during the pregnancy period. The structure of the present invention facilitates transfer of the nurturing, characteristics of the mother through dynamics, temperature, graphical imagery, sound, scent, and nourishment to the infant, baby, toddler, or child whereby each senses the replicated comfort, attachment, and/or bonding the mother, as in the womb.

14 Claims, 11 Drawing Sheets

FIG. 1

(56) References Cited

U.S. PATENT DOCUMENTS

| | | | |
|---|---|---|---|
| 2009/0064415 A1* | 3/2009 | Payne | A47C 19/126 |
| | | | 5/620 |
| 2010/0030122 A1* | 2/2010 | Gaspard | A61H 7/004 |
| | | | 601/136 |
| 2012/0131748 A1* | 5/2012 | Brykalski | A47C 21/044 |
| | | | 5/423 |
| 2013/0019407 A1 | 1/2013 | Sheppard | |
| 2015/0045608 A1* | 2/2015 | Karp | A41B 13/065 |
| | | | 600/28 |
| 2015/0282631 A1* | 10/2015 | Creamer | A47C 21/06 |
| | | | 5/423 |

* cited by examiner

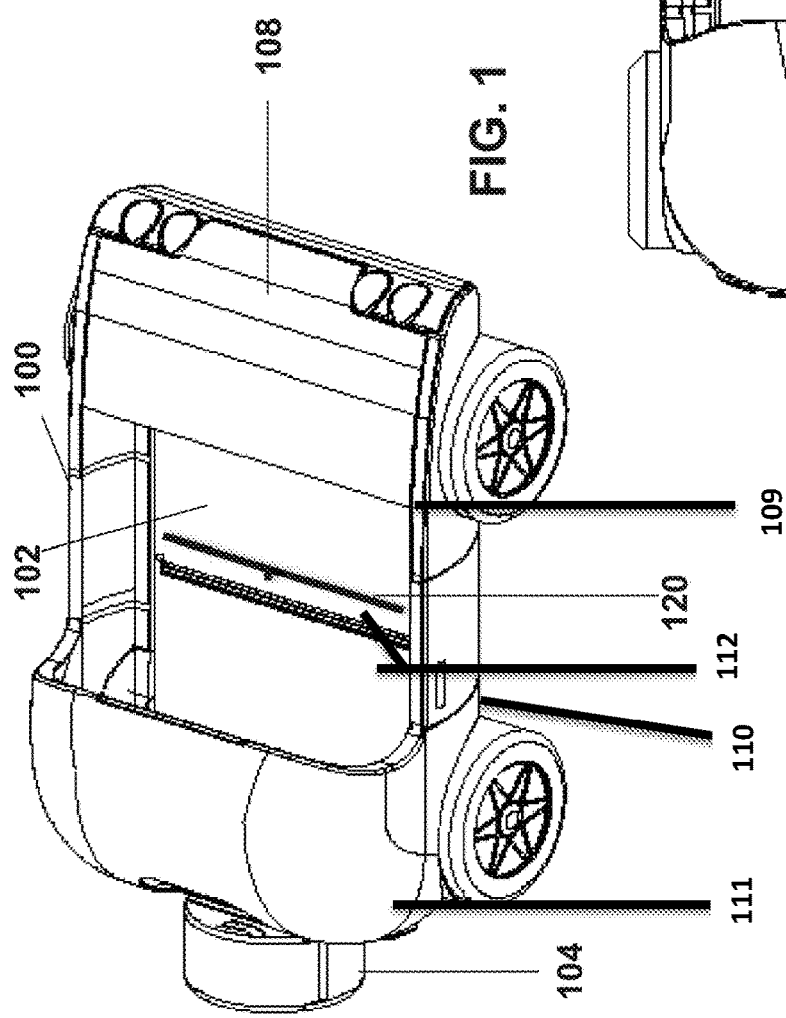
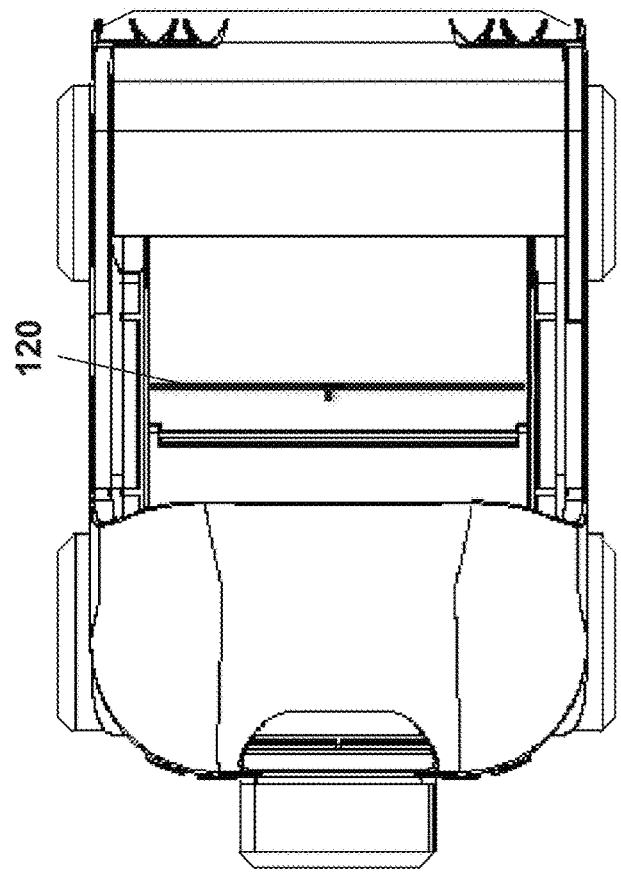
FIG. 1
FIG. 2

INFANT, TODDLER AND CHILD SENSORY ENHANCING BED

CROSS-REFERENCE TO RELATED APPLICATION

This formal utility patent application is related to provisional patent application No. 61/929,499 filed on Jan. 4, 2014. The contents of both applications are incorporated herein by reference.

FIELD OF THE INVENTION

This God-inspired invention relates to multi-direction motion bed. In particular, this invention relates to a bed for infants, babies, toddlers and children having the capability to move in multiple directions thereby providing relaxation and a comforting feeling within the bed. In addition to the multiple motion movements, this present invention comprises temperature controls, audio/visual capabilities, scent ventilation and a bottle warming apparatus for convenient feeding. It is also equipped with a multidirectional restraining element and/or seat belt for their security. This sensory enhancing bed is an external replication that simulates the internal physiology of a mother's womb through the perception of the five senses—touch, taste, smell, sound and sight, whereby each feature provides for the care, comfort and convenience of the infant, baby, toddler or child. In so doing, sensory enhancing bed helps them to calm down, relax, stop crying and simply go to sleep. This present invention can come with or without some of the aforementioned features.

BACKGROUND OF THE INVENTION

Infants, babies, toddlers and children are in most instances challenged by their inability to effectively communicate their needs verbally. As a result, more often than not they cry out desperately to signal that something is wrong. Parents, guardians and caretakers become perplexed on determining how to solve their challenge and meet their needs. One such challenge is to get them to calm down and relax, stop crying and simply go to sleep. Over the years, there have been numerous actions that have proven to be affective. These methods involve using each of the five senses, starting with sense of touch, being comprised of motion, movement and temperature. The remaining four senses taste, smell, sound and sight are also used.

The objectives within this patent are two-fold: 1) to illustrate how each of these external methods described incorporate either the single or collective use of the five senses used by parents, guardians or caretakers to get infants, babies, toddlers and children to calm down, relax, stop crying and go to sleep. The second objective is to parallel how internal sensory realm perception occurs normally within a mother's womb and thereby conveniently creating an environment of care and comfort for the unborn fetus. It is documented that after birth infants, babies, toddlers and children still have an innate craving for the bonding attachment, care and comfort they experienced in their mother's womb. Their verbal unexpressed agitation causes them to become cranky and cry. The objectives contained herein will clearly explain the need that exists for this present invention, the sensory enhancing bed. It has been developed to help infants, babies, toddlers and children to calm down. Examples of some of the external methodologies are as follows.

The Sense of Touch—Motion

Beginning with the sense of touch, which is comprised of motion, movement and temperature. Countless parents, guardians and caretakers have attested to the fact that on many occasions, they were intentional about making certain that the infant, baby, toddler or child was properly bundled in the appropriate clothing before putting them in the car and taking them on a drive until they fell asleep. It is the hypnotic motion and sound of the vehicle axle tire rotation that causes them to fall asleep. The second example is cuddling and locking infants, babies, toddlers and children are also reliable methods to get them to calm down, relax stop crying and go to sleep. Rocking is particularly affective.

The rocking motion is a proven, natural sleep aid. The external rocking is the same internal motion babies feel inside their mother's womb. Nature selected this motion for its calming effect. It has positive effects on the limbic, circulatory, and other systems. It activates a deep, powerful relaxation response. Mothers intuitively rock babies using that same floating motion that occurs in the womb. Every mother knows that rocking an infant, baby, toddler or child is good for them. Further, body rocking or the repetitive and rhythmic self-rocking of a child's body, is a common method of self-soothing in young children.

Children often fall into body rocking as a method of soothing themselves, though sometimes they also body rock as a way of providing pain relief or expressing frustration. Many children softly rock in a rhythm that they find soothing when they are tired and some children do this regularly at bedtime to help themselves fall asleep. Other children do not engage in body rocking routinely but do turn to this behavior when they are experiencing physical or emotional pain. Some children may also engage in body rocking when they are frustrated and unable—or unwilling to—explain their emotions. Finally, other children body rock while humming or softly singing to themselves.

Although rocking serves as a soothing solution for infants, babies, toddlers and children, science has found that motion is also good for adults. Studies show rocking improves dreams and reduces overall stress. Rocking cures motion sickness. How the rocking motion accomplishes this is not fully understood, but it is a well proven fact. One explanation is that rocking puts accumulated toxins into circulation, and then sweeps them out. Children rarely have motion sensitivity. Yet it is found in many adults and in some instances, it gets worse with age. It is ironic that this motion sensitivity that some avoid is the actual the solution for infants, babies, toddlers and children. Various types of motion can provide this calming effect.

Beds are one way to achieve this rocking motion. Motion or rocking beds can have several features. For babies, cribs can have leg bases with curved shapes to facilitate rocking the crib. Rocking beds also exist for adults. Some features include adjustable head and foot options and basic features of a power foundation.

U.S. Pat. No. 7,478,446 to Sims describes a variable motion rocking bed is provided that includes a first support structure having a first set of pins, a second support structure having a second set of pins, and a frame, the frame capable of being in a rocking motion with respect to the first support structure and the second support structure. The rocking bed further includes a first pair of linkage assemblies secured between the first support structure and the frame, a second pair of linkage assemblies secured between the second support structure and the frame and at least one adjusting mechanism coupled to each of the first pair of linkage assemblies and to each of the second pair of linkage assemblies. At least one adjusting mechanism is operatively configured to allow the position of said first pair of linkage assemblies to vary about the width of said first support structure and engage the first set of pins and configured to allow the position of said second pair of linkage assemblies to vary about the width of said second support structure and engage the second set of pins to modify the shape of the rocking motion of said frame relative to said first support structure and said second support structure.

U.S. Pat. No. 6,682,495 to Park describes a vibrating bed comprising a basic bed having a bed frame, casters secured on the basic bed, a lateral vibrating bed plate movably ridden on the casters, a mechanism for reciprocally moving the vibrating bed plate with respect to the bed frame, a connecting rod adjusting device and tension coil springs for dampening the vibrations of the vibrating bed plate as the vibrating bed plate reaches a predetermined horizontal, or lateral, position.

U.S. Patent Application publication number 20130019407 to Sheppard describes an adjustable bed adaptable to tilt in a number of different, comfortable positions is presented. The adjustable bed comprises a bed frame, a mattress support plate, a plurality of pairs of supporting legs, a plurality of lateral leg supporting members, a plurality of elongated structures, a mattress retainer bar, a sliding member, a central cross bar, a control box, a power supply module, a remote control, a battery compartment, a back rest motor, a foot rest motor, a plurality of levers and a bed lift mechanism. The bed lift mechanism includes at least one motor claw, a left lifting leg, a right lifting leg, a left mounting bracket, a right mounting bracket and a bed lift motor. The back rest motor, the foot rest motor and the bed lift motor receives an operating signal transmitted by the remote controller and tilts the adjustable bed in the plurality of comfortable positions.

The Sense of Touch—Movement

Touch is the first sense that is developed. The mother womb is a stimulating environment where there is constant activity. The amniotic fluid is mostly water from which a rocking sensation occurs. Communication begins with sense of touch within the mother's womb through movement. Research shows that the complexity of skin has 100 varieties of cells that are sensitive to heat, cold, pressure and pain. The first motion that occurs is the heart beat after only 3 weeks of conception. Between 6 and 10 weeks, fetal babies' burst into motion with stretching and rotational movement of the head, arm and legs. After 10 weeks, they are able to swallow and move spontaneously based their individual need and interest as they become more sensitive to their internal environment.

A variety of internal and external factors can dramatically influence a person's ability to sleep. In addition to motion, another factor that can influence one's ability to sleep is temperature. The thermal environment is a key determinant of sleep because thermoregulation is strongly linked to the mechanism regulating sleep. Excessively high or low ambient temperature may affect sleep even in healthy humans without insomnia. Research shows that the ideal temperature range for sleeping varies widely among individuals. People simply sleep best at the temperature that feels most comfortable. Extreme temperatures in sleeping environments have the tendency to disrupt an individual's sleep. Rapid Eye Movement (REM) sleep is commonly more sensitive to temperature-related disruption.

Human beings are warm-blooded and able to maintain their own body temperature independent of their outside environment. Because of thermoregulation, there is a natural physical balancing of heat loss, with heat production in our bodies. When an adult gets hot, the body sweats to compensate and cool down. When a person's body temperature drops, they shiver and move around to increase their metabolism and therefore their body heat. Infants, babies, toddlers and children have only a limited ability to regulate their own body temperature. As a result, their external environment is always critical, but it is especially critical when sleeping. One conventional way to control an infant, baby, toddler or child's temperature in bed is through their clothing and external coverings such as blankets.

The Sense of Touch—Temperature

Some parents, guardians and caretakers place infants and babies in dresser drawers that are proportionally befitting in height, length, depth and width. They align the entire inner perimeter of the drawers with blankets and also place blankets atop of the infant or baby. In their efforts, they were attempting to create an encapsulated environment for warmth.

Another method used to create warmer temperatures is an operable clothing dryer. Infants and babies are placed in bassinets then covered with blankets and placed on top of a running dryer. In this method, it is a combination the heated temperature, vibration movement and sound that cause the infant/baby to fall asleep. Also, swaddling infants and/or babies is another method that makes them feel warm and secure. However, none of these approaches to control their temperatures and help them fall asleep focus on regulating the temperature of the bed or crib in which they are sleeping. Research indicates the unborn fetus reacts to hot and cold temperatures with responsive movement that occurs when hot or cold objects are placed on the mother's abdomen. The temperature in the mother's womb is approximately 38 degrees Celsius. At birth, the newborn finds him/herself suddenly in a colder environment. They immediately lose heat as they leave the warmth of their mother's womb. The heat loss is due to the evaporation of amniotic fluids from the newborn's body. Newborns cannot regulate their own temperatures. Therefore proper thermal protection is crucial at birth and in the first days of life to ensure that the newborn does not become either too cold or overheated. If heat loss is not prevented, the newborn will develop hypothermia—subnormal body temperature. This causes sickness and increases the risk of developing more severe health problems or even death. It is also important to make certain that they do not become overheated. Whereas, hyperthermia-increased body temperature may be caused. Both are equally dangerous.

The Sense of Taste

Unborn babies are constantly being nourished while within their mother's womb. This is where true comfort food originated. Eating is pleasurable and both soothing as well as relaxing. Proper nutrition regulates our blood sugar which has a calming effect. Infants, babies and toddlers become calm and relaxed by the smell and taste of their mother's breast milk. This is why often times after eating they become sleepy. Giving infants, babies, toddlers and children warm milk is a method used to get them to relax and go to sleep. As the amino acid within the milk is heated, they become a natural tranquilizer. Many adults still utilize this method to also help them calm down, relax and go to sleep.

The Sense of Smell

The nose develops between 11 and 15 weeks. Chemical compounds cross the placenta and join the amniotic fluids providing the fetus with the senses of taste and smell. The nasal chemoreceptive system is comprised of four systems: 1) the main olfactory; 2) the trigeminal; 3) the vomeronasal;

and 4) the terminal system. These systems provide complex olfactory input to the fetus. The smell of their mother's breast mild has a calming effect on infants and babies. These are the external methods taken by parents, guardians and caretakers pertaining to the sense of smell. Aroma therapeutic scents have also proven to be highly effective for their tranquil calming effects. Mothers have taken portions of their clothing and attached them to infants, babies, toddlers and children as a means to sooth them. The mother's aroma causes them to feel secure which is comforting. The use of scented candles, fragment potpourri, and essential oil are additional methods that have been used to help infants, babies, toddlers and children as well as adults to relax.

The Sense of Sound

It has been proven that certain sounds have relaxing calming effects. The sounds that sooth are varied and range from hypnotic repetitive humming tones to delicate lullabies, tranquil fluid, oceanic sounds and classical music compositions the name a few. Using rhythmic sounds is another practice that is used as a calming method. Parents, guardians and caretakers also do such things as recording the mother's voice and placing it close to the infant, baby, toddler and child. Some have operated/recorded vacuum cleaner/hair dryer sounds. Each of these methods work and have a calming influence to relax the infant, baby, toddler and child to get them to go to sleep.

Research suggests that there is a built-in rhythmic sound within the mother's womb that occurs from the blood swishing through the arteries. Amniotic fluids, embryonic membranes, the uterus and the maternal abdomen shield the fetus from the outside world, however, sound vibrations and emotions still simulate the fetus. Additional research concludes that the fetus can hear outside voices. A mother's voice is transmitted through her body to the womb. For this reason, her voice is more powerful and stronger than any other outside voices or sounds. It has been proven that sounds impact the fetal heart rate. Studies indicate that certain masial sound causes a change in metabolism.

The development of hearing is complex. At 16 weeks reactive listening begins, however, this is 8 weeks before the structure of the ear is complete, which takes 24 weeks to fully develop. It is amazing that receptive hearing starts developing with the skin and skeletal framework. Responsive hearing develops at 16 weeks.

The Sense of Sight

The use of audio and visual equipment is another method used to calm infants, babies, toddlers and children. Research suggests that reading, viewing educational games, playing musical videos or watching television helps to stimulate the brain. When the brain is stimulated for a prolonged period of time, it is this active engagement that makes one feel tired and want to go to sleep. The audio/visual methods works in unison to provide sound and sight to distract and calm the infant, baby, toddler and child.

Ceilings mounted colorful mobiles captivate their attention and consequently relaxation occurs. Parents, guardians and caretakers often select paint colors that have a calming effect as a means to provide comfortable environments for infants, babies, toddlers and children. Certain colors provoke emotional and physical responses. Colors are classified as either warm and stimulating (red, pink orange and yellow) while blue, green and purple colors are cooler in tone which makes them the most relaxing. Relaxing colors have a soothing effect on the mind and body. Studies point to the fact that vision evolves during gestation and when light is projected on a mother's abdomen, the fetus heart rate accelerates. Research further indicates that the unborn fetus has some form of sight. Upon observation, they have the same facial gestures and movements when they dream as that of adults who dream. The sense of sight becomes predominant after birth, however, studies show that the premature babies show visual focus between 28 through 32 weeks, and at 33-34 weeks their visual attention is equivalent to babies of 40 weeks. Prenates with their eye lids still fused use some aspect of vision to detect the location of needles entering the mother's womb by flight-shrinking away from them or fight-attacking the needle with a fist.

Research indicates that Sudden Infant Death Syndrome (SIDS) is the leading cause of death in infants for the first 30 days following birth. There are physical and sleep environmental reasons that contribute to an infant or baby's vulnerability. Some of the physical factors are as follows: 1) Brain abnormalities—the portion of the brain that controls breathing and arousal from sleep does not properly work. Examination of the brain stems indicates that there is a developmental delay in the formation and function of serotonin, which bind nerve pathways to the brain. Also, there is a delay in the development of nerve cells within the brain that are critical to normal heart rate and lung function. 2) Low birth weight in premature and multiple birth babies increases the likelihood that the brain has not matured completely. As a result, these babies have less control over the automatic processes such as breathing and heart rate. 3) Respiratory infections contribute to breathing problems when infants have a cold. 4) Larynged, chemoreflex, nerve cell pathways located in the back of the throat (pharyn) and within the voice box along with upper airways reflexes regulate changes in heart rate and blood pressure. When the airway is stimulated by saliva or regurgitated stomach contents, saliva in the airways activates this reflex and triggers swallowing. When infants rollover and/or are placed on their stomachs to sleep face down, their reflexes are diminished and swallowing is decreased. Air movement around the mouth may be impaired and may cause the infant and/or baby to breathe in the carbon dioxide they just exhaled. The facedown sleeping position on their stomachs or even sleeping on their sides causes more difficulty in breathing than those placed their backs. Infants and/or babies that sleep along side another person are at a higher risk of unintentional smothering. Furthermore, placing soft surfaces such as fluffy comforters, waterbeds, couches, sofas, pillows, quilts, sheepskins or blankets around the baby can block their airways. The Comfy Cruiser™ bed was designed to conveniently care for and comfort infants, babies, toddlers and children. The purpose of the multidirectional restraining seatbelt element featured is to keep them from repositioning themselves on their stomachs and/or side which causes difficulty in breathing. Also to secure the placement of the back sleeping position in order to help prevent one of the sleep environmental factors that causes Sudden Infant Death Syndrome.

Motion, temperature, sight, sound, scent and taste are stimulating determinants within a mother's womb. However, no current product provides features that are equipped with motion, temperature, sight, sound, scent and feeding features. There remains a need for a product that conveniently embodies and provides these features in a caring, comforting environment for infants, babies, toddlers and children.

SUMMARY OF THE INVENTION

The present invention is a device or structure that provides sensory enhancement for the care, comfort and convenience of the infant, toddler, or child. The invention replicates the physical, physiology, and sensation of the mother to the child during the pregnancy period. The structure of the present invention facilitates transfer of the nurturing, characteristics of the mother through dynamics, temperature, graphical imagery, sound, scent, and nourishment to the infant, baby, toddler, or child whereby each sense replicates care, comfort, attachment, and/or bonding to the mother, as in the womb.

The present invention comprises a bed structure that can be configured in shapes and models of various transportation vehicles. This bed has the capability to perform various motions that resemble the motion of a rocking chair or hammock. The bed can be controlled to produce movements in various directions. The present invention also comprises the capability to control the temperature in the bed. The motion and temperature controls work to simulate the conditions in a mother's womb.

The present invention can also combine features of motion, temperature, sight, sound, and scent into one system that simulates a mother's womb and provides a soothing environment for an infant, baby, toddler or child.

DESCRIPTION OF THE FIGURES

FIG. 1 is a top, front and side view of a motor vehicle bed structure embodiment of the present invention showing its nominal features, and internal accommodations for the infant, baby, toddler, or child.

FIG. 2 is a top view of a motor vehicle bed structure embodiment of the present invention showing the reclining and horizontal configuration of the bed area for the infant, baby, toddler, or child.

Figure 3:
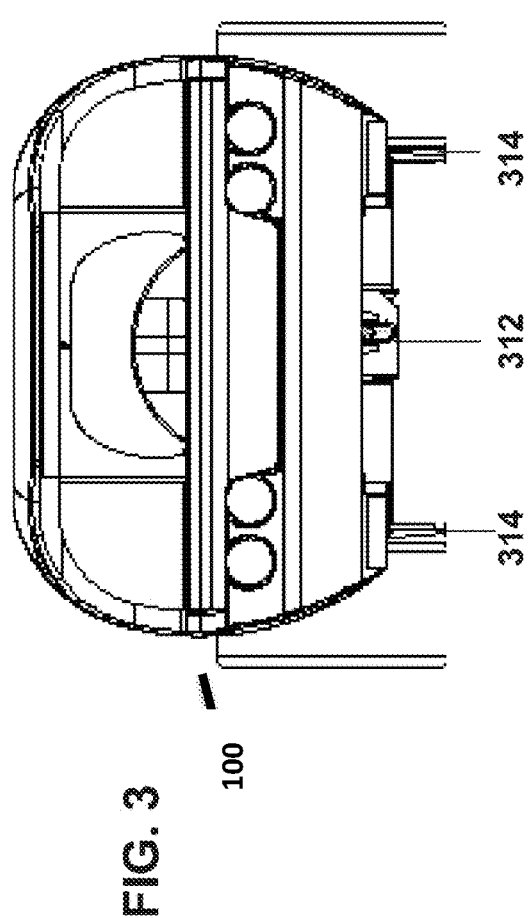
FIG. 3 is a front view of a motor vehicle bed structure embodiment of the present invention showing a mechanical system for creating various movements of the bed structure embodiment.

An embodiment of the present invention can also comprise audio visual capabilities in the form of a computer tablet to provide sound and sight for the infant, baby, toddler or child while they are in their beds.

The present invention is the solution that conveniently cares for and comforts infants, babies, toddlers and children to help them calm down, relax, stop crying and simply go to sleep.

DETAILED DESCRIPTION OF THE INVENTION

The present invention, an infant, baby, toddler, or child sensory enhancing bed, is a structure comprising a unitary body. This unitary body can be in various forms. Typical forms of this body can be in the shape of a carriage, wagon, car, truck, aircraft, boat, train or other modes of transportation. This structure can also comprise motorized/dynamic mechanism(s), whereby a consoling motion of the bed structure is being represented through rotational or lateral vibration. A two part internal wall, of which one reclines, is nominally orientated horizontally and attached and/or incorporated to the unitary body structure, which allows for activities such as the sitting, sleeping, feeding diaper/underwear changing, and associated comforting of the baby, infant, toddler, or child; creating the bed characteristics/area of the present invention.

The present invention further comprises a means of controlled-heating and/or cooling that is assembled and attached to the unitary body structure and routed into the bed area for the temperature sensing (soothing) of the baby, infant, toddler or child. Graphical imaging equipment is attached to the unitary body structure for display and monitoring of the baby, infant, toddler, child, or parent to provide photo/video-graphy sensing (relaxation). The unitary body structure of the present invention can comprise attachment(s) for Audile equipment sensing (added relaxation), provided through the graphical imaging equipment or explicitly expelled through a sole mean(s). The smell sensing capabilities (calming) of the present invention are accomplished by provisions incorporated into the unitary body structure, allowing for application of individually selected aroma therapeutic scents. The unitary structure of the present invention can have a static bottle warming, and/or cup holding apparatus for nurturing/nourishing the baby, infant, toddler, or child, during any parental tactile condition.

The structure of the present invention provides the benefit of relaxation and comfort through the provision of ancillary, self-incorporated components that attend to the senses of the baby, infant, toddler, or child. The environment of the baby, infant, toddler, or child is minimally sensory amplified through, visualization (sight), aroma therapeutic scents (smell), sound, taste, and/or movement and temperature (feel) enhancements.

The present invention can comprise 5 features applicable to the senses of the infant, baby toddler, or child:

1. Imagery Sensing

The infant, baby, toddler, or child is introduced to this feature by the parent/guardian turning on a switch to activate a monitor, TV, or computer tablet. This feature has the "optional" capability of being powered by a 12V Battery, the energy source for all electrical functionality of the bed.

2. Sound Sensing

The infant, baby, toddler, or child is introduced to this feature by the parent/guardian turning on a switch to activate a monitor, TV, or computer tablet. This feature has the "optional" capability of being powered by the 12V Battery, the energy source for all electrical functionality of the Bed.

3. Taste Sensing

The infant, baby, toddler, or child is introduced to this feature by the parent/guardian turning on a switch to activate a heating medium, which transfers heat to the baby bottle in the bottle warmer (typically depicted as an external, yet attached apparatus) when the required temperature is identified by the circuited Temperature Switch.

4. Feel Sensing

The infant, baby, toddler, or child is introduced to this feature by the parent/guardian turning on a switch to activate a fan, which blows air into a Heating Ventilation & Air Conditioning (HVAC) duct, as the air is warmed or cooled (temperature functionality) by a Thermo-Electric Cooling device/module. The Thermo-Electric Cooling device/module is cooled when current flows through the device/module in normal positive and negative polarity wiring, and heated when the current flows in opposite direction (inverted polarity). The actuation (temperature functionality switching) of the Thermo-Electric Cooling device/module is determined by a circuited Temperature Controller, an identifier of the surrounding ambient temperature (atmosphere) of the space occupied by the infant, baby, toddler, or child, in the bed. A secondary means for this feature of the bed is device/module is determined by a circuited Temperature Controller, an identifier of the surrounding ambient temperature (atmosphere) of the space occupied by the infant, baby, toddler, or child, in the bed. A secondary means for this feature of the bed is represented through motion, introduced to the infant, baby, toddler, or child by the parent/guardian turning on a switch to actuate a motor (at least one) and attachment mechanism(s) (mated to the structure of the bed) that moves the bed radially (back, up, forward, or down), in the longitudinal axis (on a vertical plane) of the bed, along with a slight swaying in the lateral axis of the bed.

5. Scent Sensing

The infant, baby, toddler, or child is introduced to this feature by the parent/guardian turning on a switch to activate a fan, which blows air through the HVAC duct, across a scented pad, resulting in the scented therapeutic aroma flowing, encompassing, and filling the space, occupied by the infant, baby, toddler, or child, in the bed.

A 12V Battery is the energy source for the electrical functionalities of the Bed, however, optional for the imagery and sound sensing features. "Switched" component(s) can be left in the "ON" position, as they are powered by the activation of a motion sensor, which allows current flow to all electrical functionality of the Comfy Cruiser Bed (except the imagery and sound sensing features). The motion sensor is activated (closed circuit: ON) when the infant, baby toddler, or child is placed in the bed.

Referring to the Figures, FIG. 1 is a top, front and side view of an embodiment of the present invention wherein the unitary structure is in the form of a motor vehicle. This bed structure 100 shows nominal features, and internal accommodations for the infant, baby, toddler, or child. The sleeping surface 102 is nominally placed, and resides, in a stationary position, with the capability to be translated via remote control. Ingress of the infant, baby, toddler, or child, is motion sensed, activating some or all sensory perceptive characteristics of the bed structure 100. The bed structure 100 also has an infant multi-directional restraining element 120 similar to a seat belt device for securing an infant in the sleeping surface 102 regardless of the position of the bed structure 100 in the bed structure 100. FIG. 2 is a top view of a motor vehicle bed structure 100 embodiment of the present invention showing the reclining and horizontal configuration of the bed area for the infant, baby, toddler, or child. Also shown are the bottle warming, and/or cup holding apparatus 104. The front section 108 of the bed structure 100 can pivot upward to reveal a video screen 109. Further depicted in FIG. 1 is the rear trunk section 110 with a top portion 111 and the two part internal wall 112 of the sleeping surface 102.

FIG. 3 is a front view of a motor vehicle bed structure embodiment of the present invention showing a mechanical system for creating various movements of the bed structure embodiment. Below the front portion of the bed structure 100 (as seen in FIG. 1) is a mechanical system 312 comprised of a motor, gears and an actuator to facilitate movements of the vehicle structure to induce a desired consoling motion in the bed. The vehicle bed structure 100 rests on and is supported by support stands 314. These support stands provide stability of the bed structure during the induced motion activity. The motion produced by the mechanical system 312 is more of a lateral movement with reference to the support stands.

Figure 4:
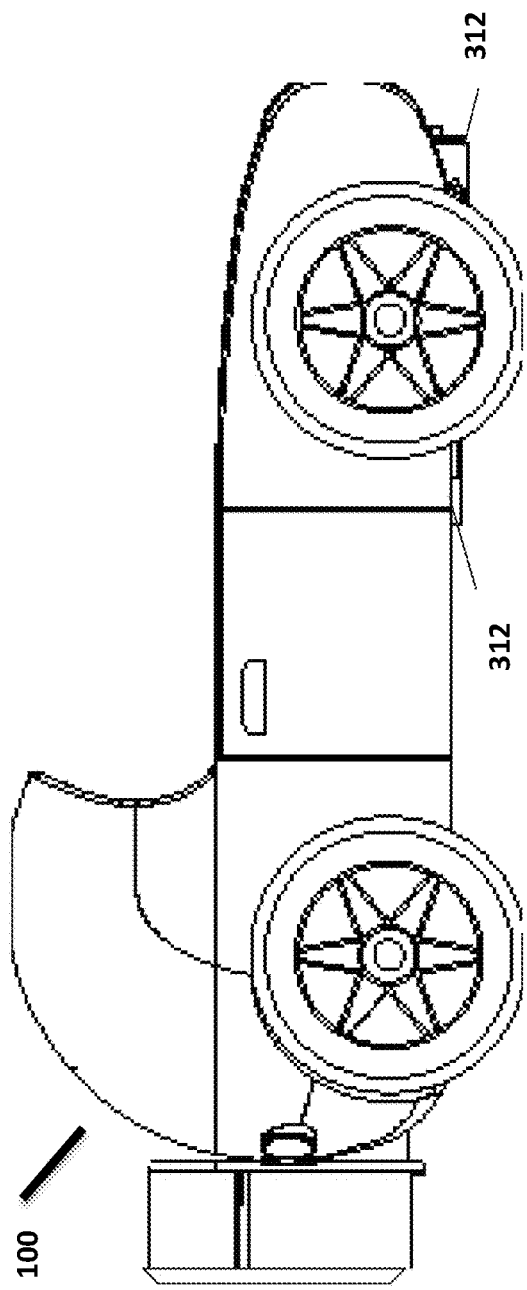
FIG. 4 is a side view of a motor vehicle bed structure embodiment of the present invention, whilst showing the supporting placement for the feeding apparatus for the infant, baby, toddler, or child.

FIG. 4 is a side view of a motor vehicle bed structure embodiment of the present invention. In this embodiment, an alternate view of the mechanical system 312 underneath the bed structure 100. In the present invention, the user can determine which direction for movements by the bed structure 100. Support stands 314 can be positioned by each of the 4 wheels on the bed structure 100.

In one embodiment of the present invention, the movements (translation or swaying/semi-rotation) of the bed structure 100 are accomplished by positioning atop a base structure that lies on the ground, for support of the whole bed assembly. The body has two opposingly biased pins horizontally orientated (see FIG. 12), that complements slots on the base structure, allowing for pivoting in either the forward and aft-like translation, or the left and right-like swaying movement. The base structure is also designed with slots and routes/path, accepting of pins on the relocatable actuator to follow, which determines the movement of the bed.

Figures 5, 5A:
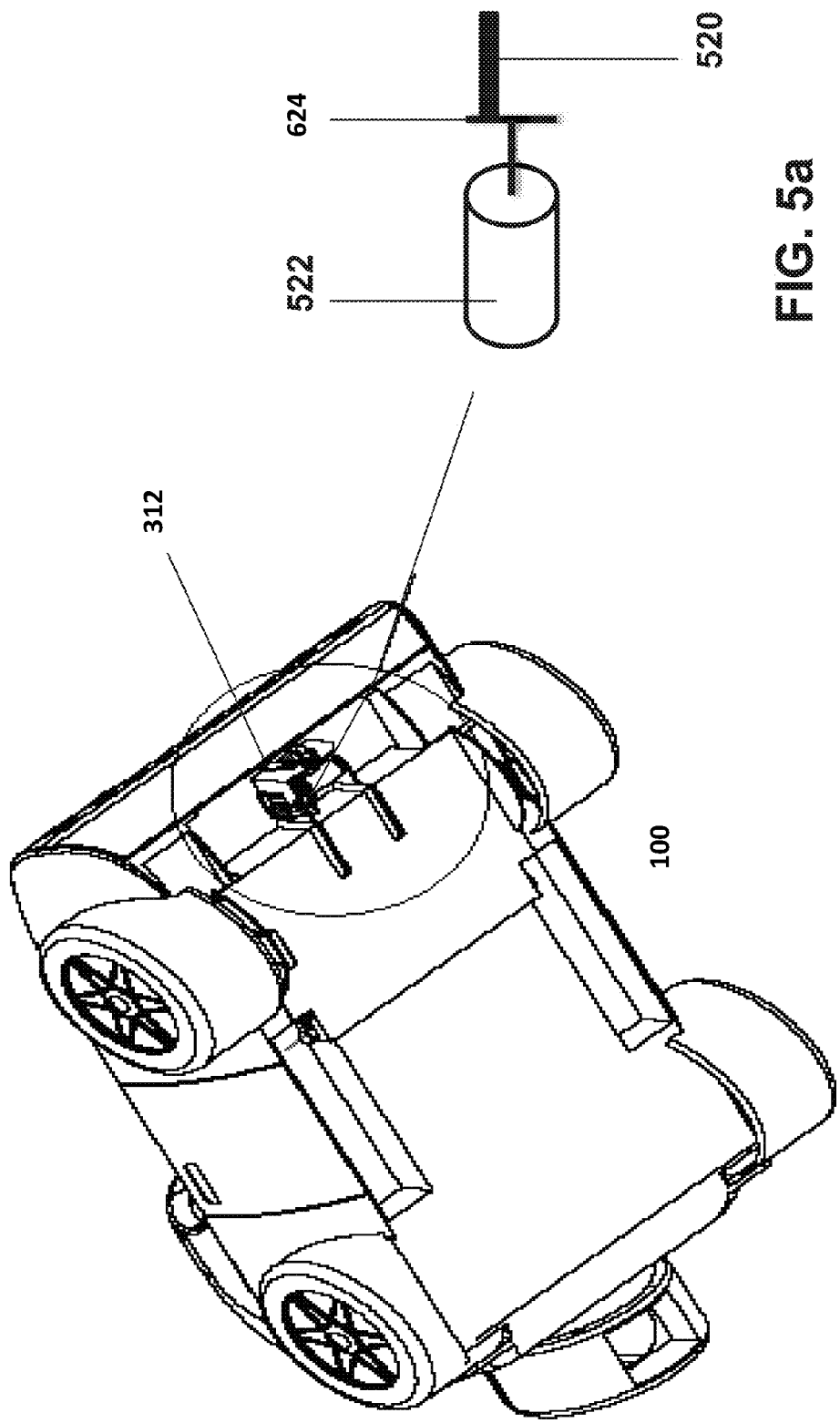
FIG. 5 is a bottom view of a motor vehicle bed structure embodiment of the present invention showing a mechanical system for creating various movements of the bed structure embodiment.
FIG. 5a is a view of a general motor and gear system for use in the present invention for creating various movements of the bed structure embodiment.

FIG. 5 is a bottom view of a bed structure 100 of the present invention showing the mechanical system 312 for creating various movements of the bed structure 100.

Figure 6:
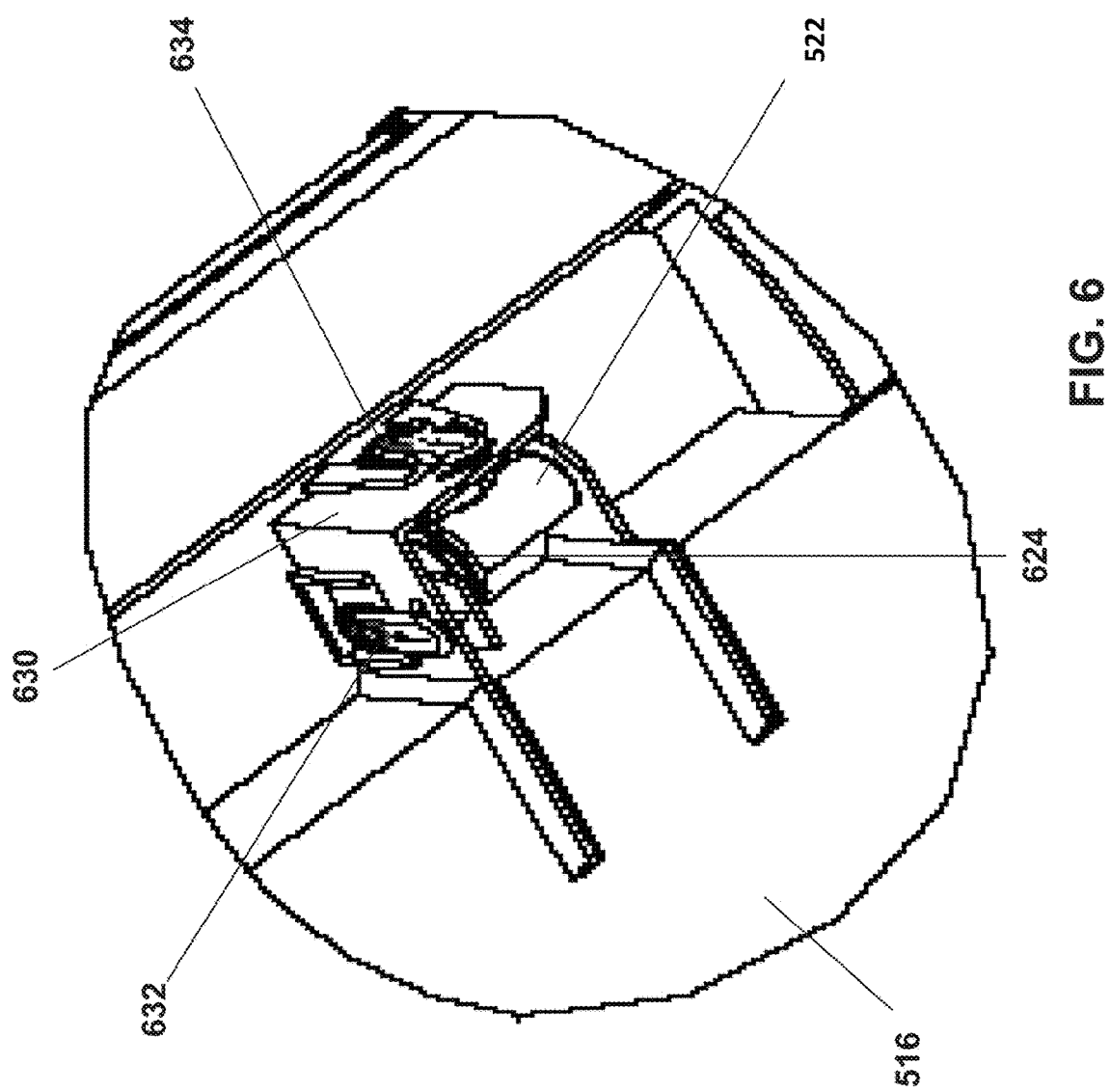
FIG. 6 is a magnified view of the motor and gear system for use in the present invention for creating various movements of the bed structure embodiment.
Figure 7:
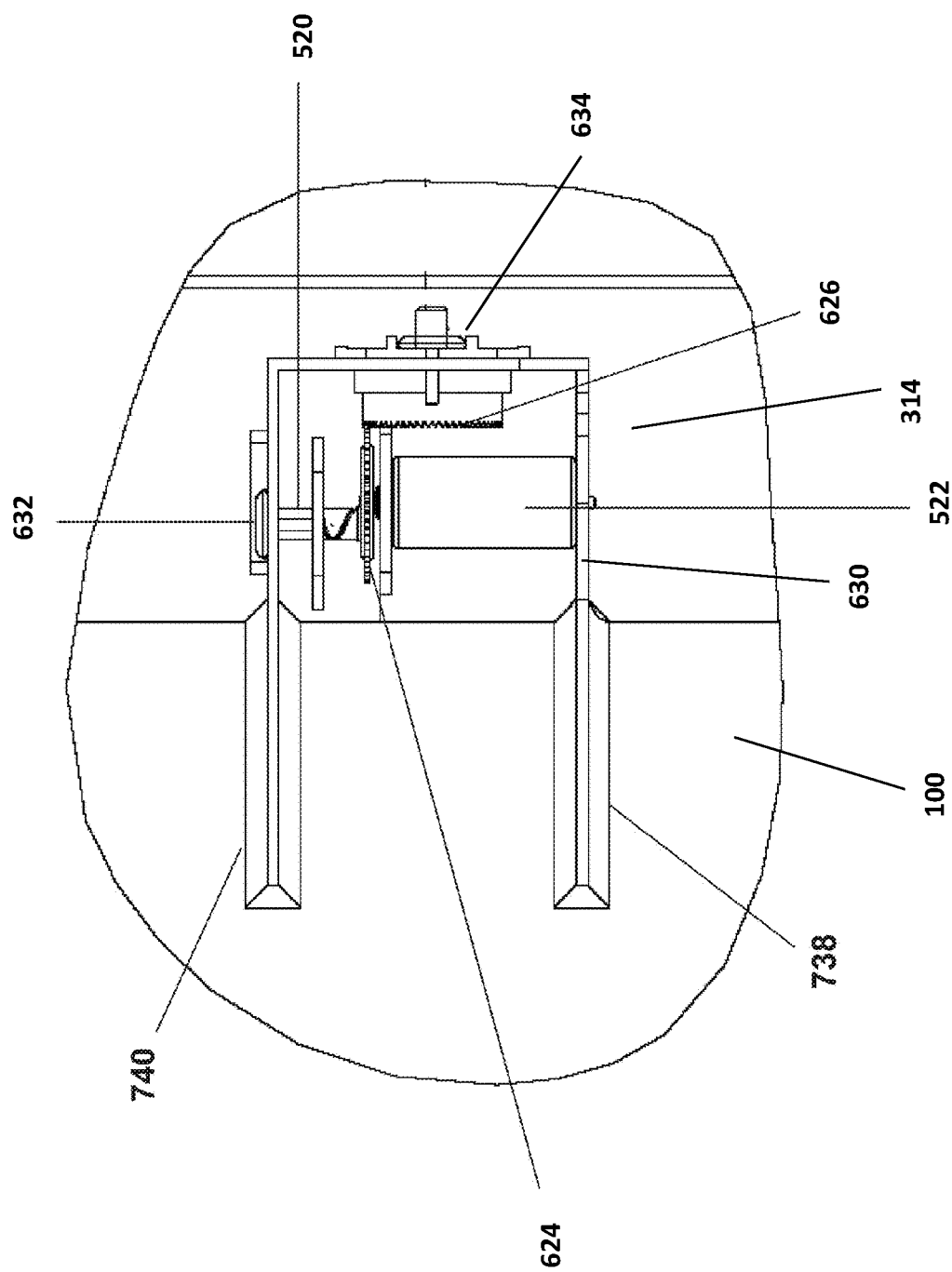
FIG. 7 is a schematic view of the motor, gear and actuator system for use in the present invention for creating various movements of the bed structure embodiment.

FIG. 6 is a magnified view of the mechanical system 312 for use in the present invention for creating various movements of the bed structure embodiment. As shown, a motor 522 connects to a first gear 624. A first actuator 632 connects to the first gear 624 to facilitate movements of the bed structure 100. First gear 624 also connects to second gear 626 (as shown in FIG. 7). A second actuator 634 connects to second gear 626 to facilitate lateral movements of the bed structure. A housing 630 facilitates translation motions between the bed structure and actuators.

Figure 9:
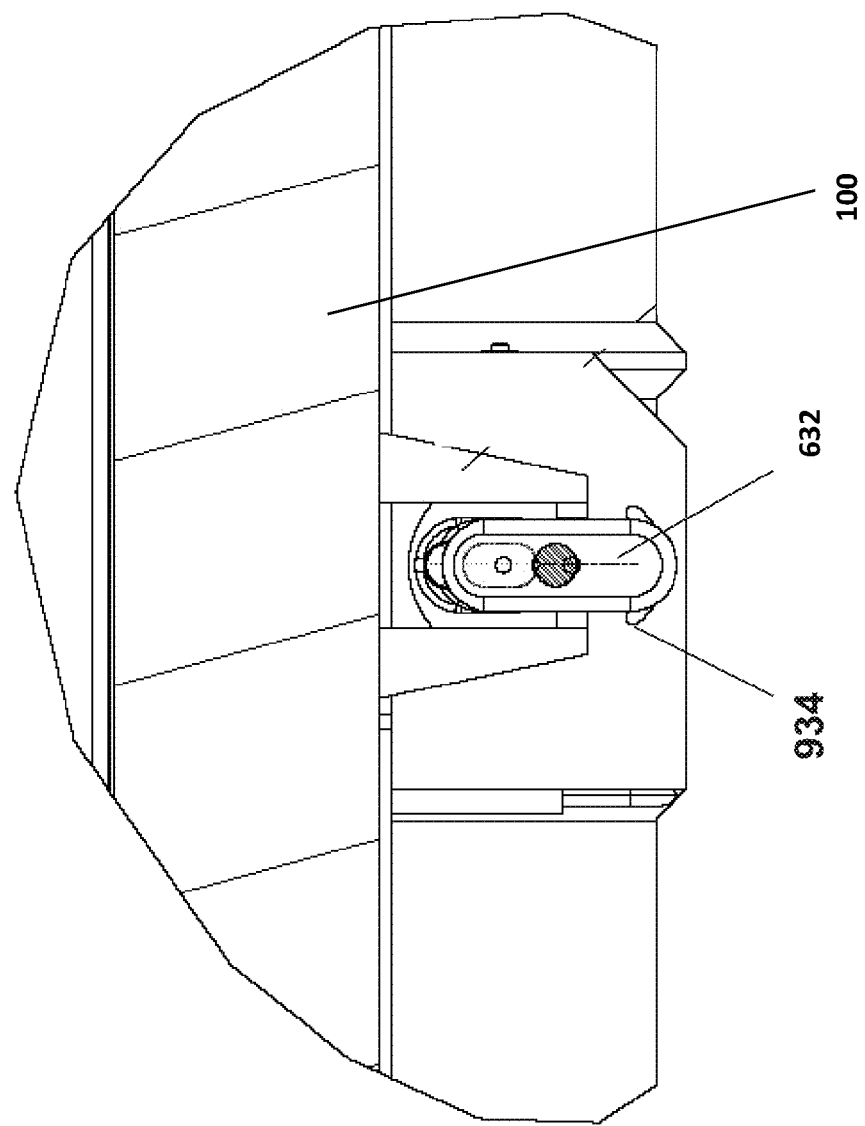
FIG. 9 is a view of a front positioned actuator system of the present invention for generally horizontal movements of the bed structure of the present invention.
Figure 10:
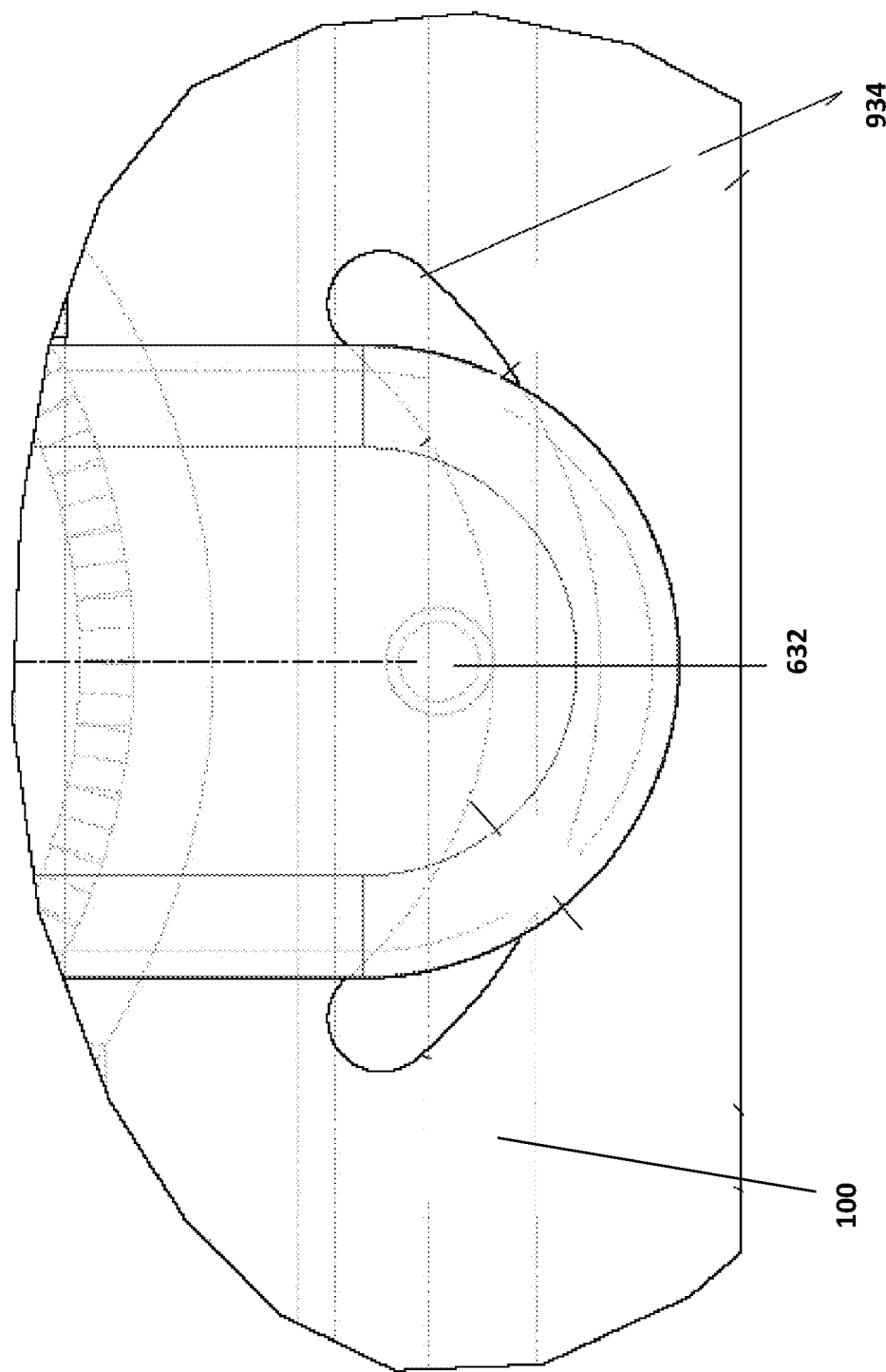
FIG. 10 is a view of a groove path for guiding the movement of the front actuator during the movement of the vehicle structure of the present invention.

FIG. 5a and FIG. 7 show schematic views of the mechanical system 312 for use in the present invention for creating various movements of the bed structure 100. Shown in FIG. 7 are two brackets 738 and 740 that attach the mechanical system 312 to bottom of the bed structure 100. The motor 522 is positioned inside the housing 630. In this configuration, the first gear 624 attaches directly to the motor 522. First rod 520 is attached to the first gear 624 and is also attached to the first actuator 632. First actuator 632 is positioned to move within a parabolic groove (path) 934, as shown in FIG. 9 and FIG. 10. This parabolic groove path 934 is on the side of the bed structure 100. Movement of the first actuator 632 will cause the bed structure to move. Parabolic groove path 934 dictates a forward and aft-like translation or movement. In FIG. 7, first gear 624 engages second gear 626. Second gear 626 faces the front of the bed structure 100 and connects to second actuator 634.

Figure 8:
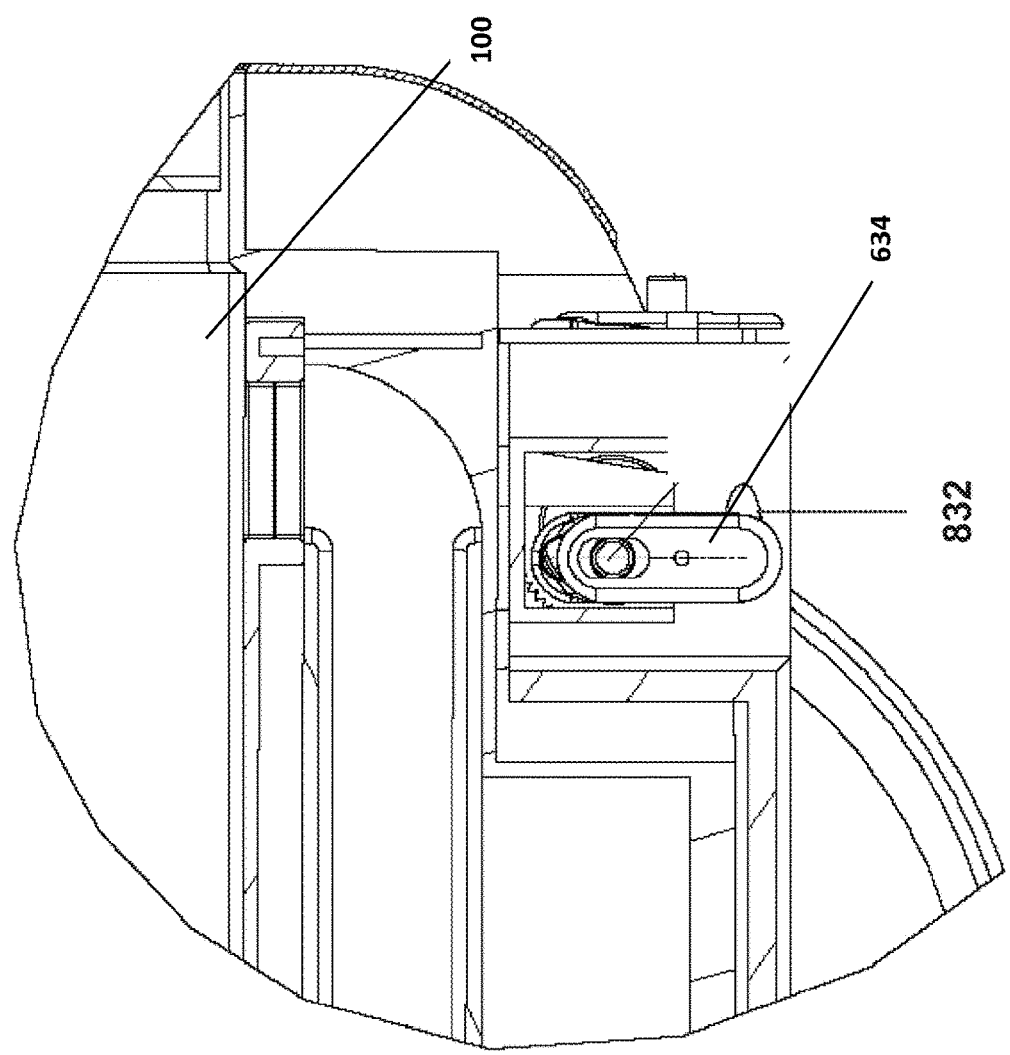
FIG. 8 is a view of a side positioned actuator of the present invention for generally vertical movements of the bed structure of the present invention.
Figure 12:
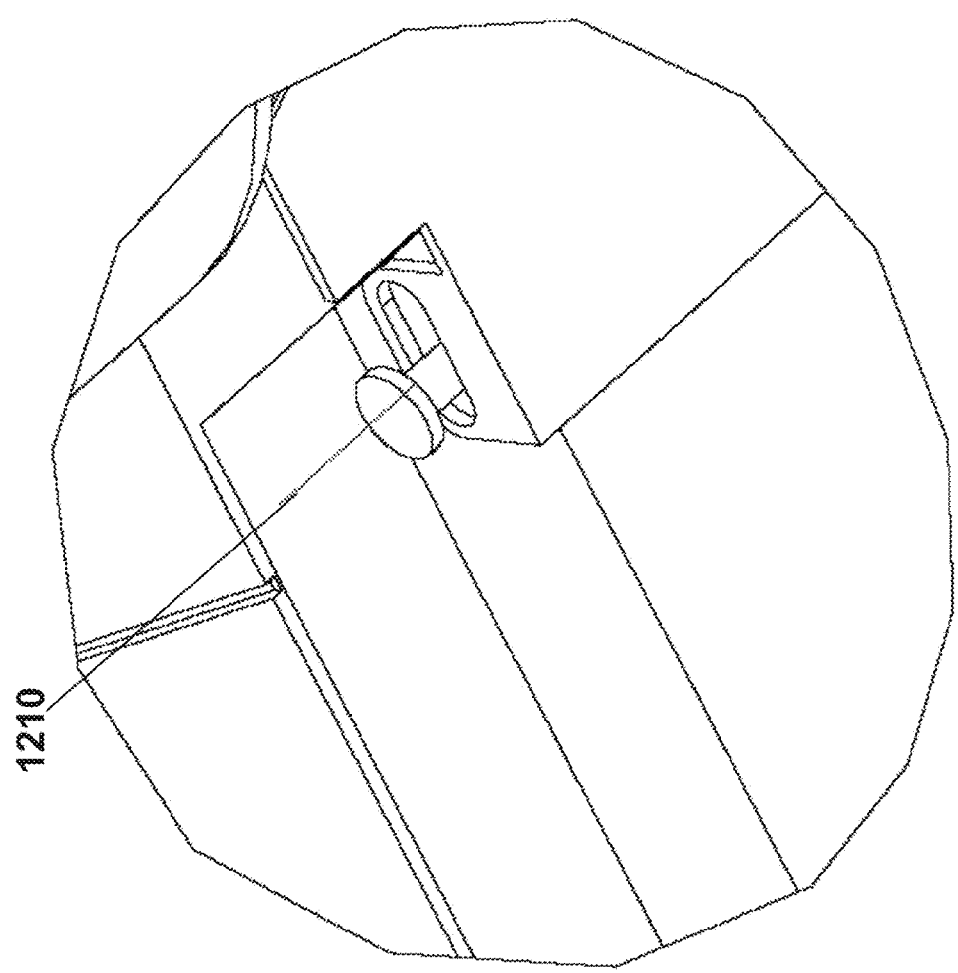
FIG. 12 is a view of a pivot pin for facilitating the engagement of the vehicle structure with the mechanical system of the present invention.

FIG. 8 and FIG. 12 show views of the front positioned second actuator 634 of the present invention for left and right-like movements of the bed structure 100 of the present invention. The second actuator 634 follows an elliptical groove path 832 to produce the left and right-like translation motion.

Figure 11:
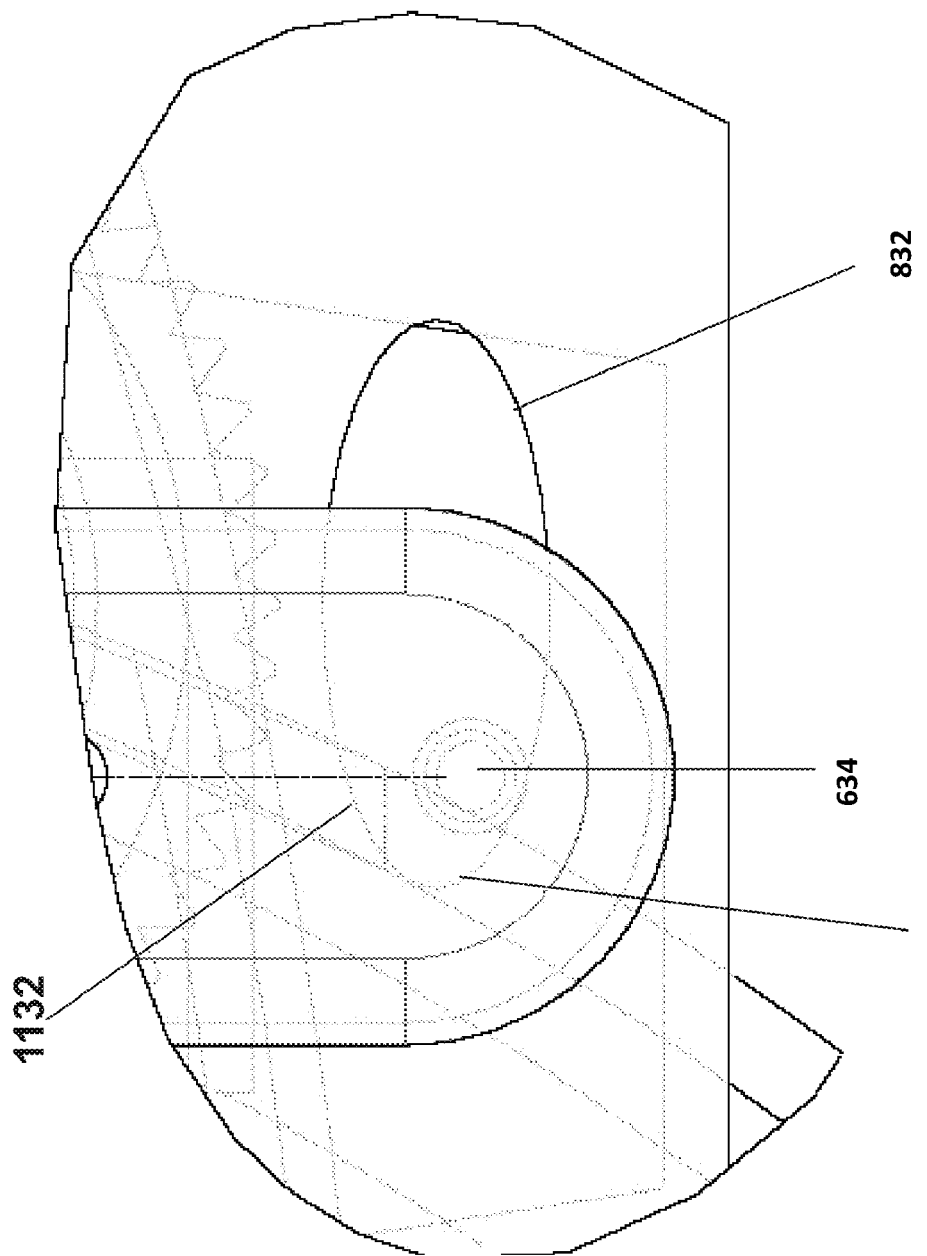
FIG. 11 is a view of a groove path for guiding the movement of the side actuator during the movement of the vehicle structure of the present invention.

FIG. 10 is an enlarged view of the parabolic groove path 934 for guiding the forward and aft-like movement of the first actuator 632 during the movement of the bed structure 100 of the present invention. FIG. 11 is an enlarged view of the elliptical groove path 832 for guiding the left and right-like movement of the second actuator 634 during the movement of the bed structure 100 of the present invention.

FIG. 12 is a view of a pivot pin 1210 for facilitating the engagement of the bed structure 100 with the mechanical system 312 of the present invention. As mentioned, the bed structure 100 has two opposingly biased pivot pins horizontally orientated (see FIG. 12), that complements slots on the base structure, allowing for pivoting in either the forward and aft-like translation, or the left and right-like swaying movement.

The structure of the present invention can be made in whole, or at least in part, of plastic, corrosion resistant metal, weather-resistant wood, rubber, and/or composite material construction, whilst providing a means for the enhanced sensory perception (all five senses) of the infant, baby, toddler, or child. The shape or geometrical design (external) of said structure embodied in the present invention is liken to, but is not limited to, a mode of transportation (carriage, wagon, car, truck, aircraft, boat or train; with/out ancillary doors) withstanding it allows for the incorporation of the sensory enhancing provisions required by the scope of the present invention.

In addition to the above-described method and structure for creating motion for the bed structure, other systems that generate bed movement are also available for implementation of the present invention. The present invention provides the capability to select a particular bed movement by engaging and disengaging certain gears in the motor assembly. However, a user can generally accomplish the same objectives of the present invention with single movement bed systems.

In addition to the motion, the present invention also comprises the use of temperature controls. Similar to motion, temperature can also have a relaxing, calming effect. As mentioned, in one embodiment, a switch can activate a fan, which blows air into an HVAC duct in the bed structure. As the air travels it is warmed or cooled (temperature functionality) by a Thermo-Electric Cooling device/module. Other temperature control means can include a blanket with temperature adjustment capabilities. Also the bed/mattress can have temperature adjustment capabilities. Other conventional heating and cooling means can also be implemented to accomplish the temperature control function.

Figure 13:
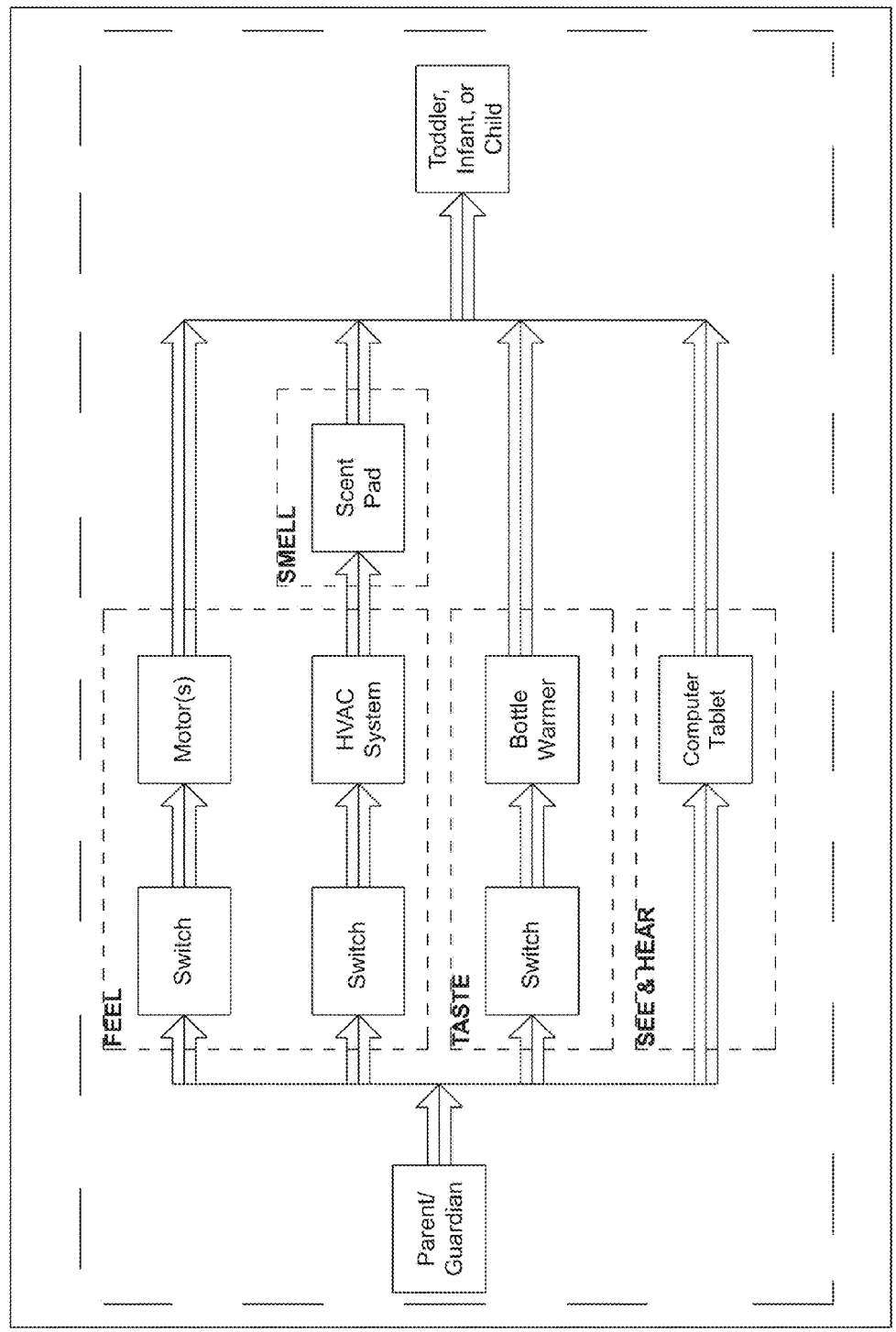
FIG. 13 is a view of a system schematic of the components in the system of the present invention.

FIG. 13 is a view of a system schematic of the components in the system of the present invention. Shown is the parent/guardian that has the ability to control the different functions in the enhanced bed of the present invention. Parallel systems have controllers/switches that separately control the feel, smell and taste functions. The parent/guardian also has the capability to control the sight and sound (audio/visual) function. The feel function relates primarily to the movements of the enhanced bed as indicated by the motor(s) and the temperature control. The scent pad function can also be controlled by the temperature controller. The taste function incorporates the bottle warmer. All of these mentioned functions and system capabilities of the present invention are directed at providing a comforting and cuddling environment for the infant, baby, toddler, or child.

An additional embodiment of the present invention can comprise the capability for a parent or guardian to monitor the activities of the baby, infant or child while not in the same room or vicinity of the baby, infant or child. This embodiment can comprise the features in the sensory bed of the present invention. In addition, in this embodiment the video screen used to provide audio/visual capabilities can have camera means that can capture images of the baby, infant or child in the sensory bed. These images can be transmitted to a receiver device that the parent or guardian can use to view the activities of the baby, infant or child while in another room. As a result, this alternate embodiment can provide monitoring capabilities for the parent. To facilitate the capturing of images at the sensory bed, the audio/visual screen can comprise a computing device such as a computer tablet. This tablet would have the capability to communicate with other electronic computing devices such as computers and smart phones. Further, the camera capabilities of the audio/visual device could be similar to camera devices attached to computer screens.

In still another embodiment of the present invention, there can a controller element that can control the functions of the present invention including the bed movements, temperature, aroma and audio/visual capabilities of the invention. The user (i.e. a parent) could program desired parameters for each function including a set time for each function to operate. The user can also receive status information for each function and remotely control the functions' operations. For example, if the parent receives an image that shows the child is asleep, the parent could remotely turn off functions such as the audio/visual function. The user can also have a time set to automatically shut off a function. The audio function of the present invention can also have the capability to provide various sounds without the visual component. For example, these sounds can include the sound of a vacuum cleaner running; rain drops falling, train sounds and various types of music. These different types of sounds can be stored and indexed in the audio/visual device. If the user just desired sounds, they could select "sound only" and then select the desired sound from the sounds in the index.

Still, another alternate embodiment of the present invention is designed to accommodate an animal such as a person's pet.

The enhanced child sensory bed of the invention provides significant advantages over the current art. The invention has been described in connection with its preferred embodiments. However, it is not limited thereto. Changes, variations and modifications to the basic design may be made without departing from the inventive concepts in this invention. In addition, these changes, variations and modifications would be obvious to those skilled in the art having the benefit of the foregoing teachings. All such changes, variations and modifications are intended to be within the scope of this invention.

I claim:

1. A sensory enhancing bed comprising:
 a bed structure comprising a bed frame, said bed structure designed to be partially enclosed;

a sleeping surface positioned on said bed frame and capable of supporting an infant, baby, toddler, or child;

a mechanical system attached to said bed structure configured to provide multidirectional movement of said bed structure, the mechanical system comprising a motor, a first actuator attached to a first gear wheel, said first actuator fitting through a parabolic guide path that facilitates a forward and aft parabolic swaying movement, a second actuator attached to a second gear wheel, said second actuator fitting through an elliptical guide path that facilitates side to side swaying movement, wherein the motor is adapted to provide rotational movement to the first gear wheel to rotate the first actuator and adapted to provide rotational movement to the second gear wheel to rotate the second actuator; and a temperature control system attached to said bed structure, said temperature control system comprising a fan, a heating ventilation and air conditioning (HVAC) duct, a thermoelectric device and a scent pad, wherein the temperature control system is configured to activate said fan to blow temperature controlled air and to provide a therapeutic aroma through the HVAC duct and across the sent pad to adjust a temperature and provide a therapeutic aroma within said bed structure.

2. The sensory enhancing bed as described in claim 1, wherein said bed structure further comprises a front section, an open middle section and a rear trunk section, said rear truck section having a top section that provides a partial cover for the bed structure.

3. The sensory enhancing bed as described in claim 2, wherein the front section is capable of pivoting in an upward direction to an open position, said front section comprising a video screen.

4. The sensory enhancing bed as described in claim 3, wherein said video screen is attached to an inside surface of the front section such that when said front section is in the open position, the video screen is visible inside said bed structure.

5. The sensory enhancing bed as described in claim 4, wherein the video screen is part of an audio visual device.

6. The sensory enhancing bed as described in claim 5, wherein said audio visual device is a computer tablet device.

7. The sensory enhancing bed as described in claim 1, wherein said thermoelectric device cools and warms the air blown into said bed structure.

8. The sensory enhancing bed as describe in claim 1, further comprising an infant restriction device for securing said infant, baby, toddler, or child in said bed structure.

9. The sensory enhancing bed as described in claim 8, wherein said infant restriction device is an adjustable restraining element secured to said bed structure and capable of securing said infant, baby, toddler, or child in the bed structure.

10. The sensory enhancing bed as described in claim 1, further comprising one or more support stands attached to and below said bed structure to stabilize and support said bed structure.

11. The sensory enhancing bed as described in claim 1, wherein said sleeping surface is a mattress.

12. A sensory enhancing bed comprising:

a bed structure comprising a bed frame, said bed structure designed to be partially enclosed;

a sleeping surface positioned on said bed frame and capable of supporting an infant, baby, toddler, or child;

a mechanical system attached to said bed structure for providing multidirectional movements of said bed structure, the mechanical system comprising a motor, a first actuator attached to a first gear wheel, said first actuator fitting through a parabolic guide path that facilitates a forward and aft parabolic swaying movement, a second actuator attached to a second gear wheel, said second actuator fitting through an elliptical guide path that facilitates side to side swaying movement, wherein the motor is adapted to provide rotational movement to the first gear wheel to rotate the first actuator and adapted to provide rotational movement to the second gear wheel to rotate the second actuator;

a remote monitoring and control system; and a temperature control system attached to said bed structure, said temperature control system comprising a fan, a heating ventilation and air conditioning (HVAC) duct, a thermoelectric cooling device and a scent pad, wherein the temperature control system is configured to activated said fan and blow air at a controlled temperature through the HVAC duct to adjust a temperature within said bed structure.

13. The sensory enhancing bed of claim 12, wherein the remote monitoring and control system comprises a video camera connected to the bed structure and positioned to monitor the infant, baby, toddler, or child.

14. The sensory enhancing bed of claim 13, wherein the remote monitoring and control system allows a user to control one or more of temperature, movement, scent, sound, and an audiovisual device of the sensory enhancing bed.

* * * * *